(12) United States Patent
Nakatake et al.

(10) Patent No.: US 8,748,132 B2
(45) Date of Patent: Jun. 10, 2014

(54) PROCESS FOR PREPARING INCLUSION BODY-FORMING PROTEIN

(75) Inventors: Hiroshi Nakatake, Kikuchi (JP); Akihiro Meta, Kikuchi (JP); Kiyotaka Suenaga, Kikuchi (JP); Masaki Hirashima, Kikuchi (JP); Hiroaki Maeda, Kikuchi (JP)

(73) Assignees: The Chemo-Sero-Therapeutic Research Institute, Kumamoto-shi (JP); Teijin Pharma Limited, Tokyo-to (JP)

( * ) Notice: Subject to any disclaimer, the term of this patent is extended or adjusted under 35 U.S.C. 154(b) by 475 days.

(21) Appl. No.: 13/125,328

(22) PCT Filed: Oct. 21, 2009

(86) PCT No.: PCT/JP2009/068133
§ 371 (c)(1),
(2), (4) Date: Jul. 11, 2011

(87) PCT Pub. No.: WO2010/047347
PCT Pub. Date: Apr. 29, 2010

(65) Prior Publication Data
US 2011/0262998 A1 Oct. 27, 2011

(30) Foreign Application Priority Data
Oct. 21, 2008 (JP) .................................. 2008-270941

(51) Int. Cl.
*C12P 21/04* (2006.01)

(52) U.S. Cl.
USPC ........................................................ 435/69.8

(58) Field of Classification Search
None
See application file for complete search history.

(56) References Cited

U.S. PATENT DOCUMENTS

| | | | |
|---|---|---|---|
| 6,010,893 A | 1/2000 | Kihira | |
| 6,544,519 B1 | 4/2003 | Tokunaga et al. | |
| 2005/0221444 A1 | 10/2005 | Williams et al. | |

FOREIGN PATENT DOCUMENTS

| | | |
|---|---|---|
| JP | 2938352 | 6/1999 |
| WO | WO 98/12331 | 3/1998 |
| WO | 03 100021 | 12/2003 |

OTHER PUBLICATIONS

Gennity et al, Signal peptide mutants of *Escherichia coli*. J Bioenerg Biomembr. Jun. 1990;22(3):233-69.*
Michaelis et al, Mutations that alter the signal sequence of alkaline phosphatase in *Escherichia coli*. J Bacteriol. Apr. 1983;154(1):366-74.*
Kihira et al, Production of recombinant human matrix metalloproteinase 7 (Matrilysin) with potential role in tumor invasion by refolding from *Escherichia coli* inclusion bodies and development of sandwich ELISA of MMP-7. Urol Oncol. Jan.-Feb. 1996;2(1):20-6.*
Schottler et al, Protein engineering of the restriction endonuclease EcoRV—structure-guided design of enzyme variants that recognize the base pairs flanking the recognition site. Eur J Biochem. Nov. 15, 1998;258(1):184-91.*
von Heijne, A new method for predicting signal sequence cleavage sites. Nucleic Acids Res. Jun. 11, 1986;14(11):4683-90.*
Diane M. Retallack, et al., "Transport of heterologous proteins to the periplasmic space of *Pseudomonas fluorescens* using a variety of native signal sequences", Biotechnology Letters, vol. 29, No. 10, XP-002473228, Oct. 1, 2007, pp. 1483-1491.
E. Medina-Rivero, et al., "Modified penicillin acylase signal peptide allows the periplasmic production of soluble human interferon-γ but not of soluble human interleukin-2 by the Tat pathway in *Escherichia coli*", Biotechnology Letters, vol. 29, No. 9, XP019523935, May 4, 2007, pp. 1369-1374.
Ibrahim Ibrahimi, et al., "A Functional Interaction between the Signal Peptide and the Translation Apparatus Is Detected by the Use of a Single Point Mutation Which Blocks Translocation across Mammalian Endoplasmic Reticulum", The Journal of Biological Chemistry, vol. 262, No. 21, 1987, pp. 10189-10194.
Akihiro Iida, et al., "A signal sequence mutant defective in export of ribose-binding protein and a corresponding pseudorevertant isolated without imposed selection", The EMBO Journal, vol. 4 No. 7, 1985, pp. 1875-1880.
Dulce Soler, et al., "Zinc Content of Promatrilysin, Matrilysin and the Stromelysin Catalytic Domain", Biochemical and Biophysical Research Communications, vol. 201, No. 2, Jun. 15, 1994, pp. 917-923.
Masanori Ii, et al., "Role of Matrix Metalloproteinase-7 (Matrilysin) in Human Cancer Invasion, Apoptosis, Growth, and Angiogenesis", Experimental Biology and Medicine, (Maywood), vol. 231, 2006, pp. 20-27.
Hirotaka Haro, et al., "Up-Regulated Expression of Matrilysin and Neutrophil Collagenase in Human Herniated Discs", Journal of Spinal Disorders, vol. 12, No. 3, 1999, pp. 245-249.
Hirotaka Haro, et al., "Experimental studies on the effects of recombinant human matrix metalloproteinases on herniated disc tissues—how to facilitate the natural resorption process of herniated discs", Journal of Orthopaedic Research, vol. 23, 2005, pp. 412-419.

(Continued)

Primary Examiner — Sheridan Swope
(74) Attorney, Agent, or Firm — Oblon, Spivak, McClelland, Maier & Neustadt, L.L.P.

(57) ABSTRACT

A process for preparing an inclusion body-forming protein is provided. A nucleic acid fragment having a nucleotide sequence coding for a modified alkaline phosphatase signal peptide (modified APSP) where leucine at the 13th position in the amino acid sequence shown in SEQ ID NO: 1 is substituted with proline and/or alanine at the 21st position is substituted with the other amino acid, downstream of which nucleotide sequence is bound a nucleotide sequence of a gene of a protein of interest is also provided.

16 Claims, 3 Drawing Sheets

(56) References Cited

OTHER PUBLICATIONS

Kaoru Miyazaki, et al., "Purification and Characterization of Extracellular Matrix-degrading Metalloproteinase, Matrin (Pump-1), Secreted from Human Rectal Carcinoma Cell Line[1]", Cancer Research, vol. 50, 1990, pp. 7758-7764.

Jim Barnett, et al., "Production, Purification, and Characterization of Human Matrilysin (PUMP) from Recombinant Chinese Hamster Ovary Cells", Protein Expression and Purification, vol. 5, 1994, pp. 27-36.

Debra A. Kendall, et al., "Idealization of the hydrophobic segment of the alkaline phosphatase signal peptide", Nature, vol. 321, Jun. 12, 1986. pp. 706-708.

Takanori Oka, et al., "Synthesis and secretion of human epidermal growth factor by *Escherichia coli*", Proc. Natl. Acad. Sci. USA, vol. 82, Nov. 1985, pp. 7212-7216.

John Ghrayeb, et al., "Secretion cloning Vectors in *Escherichia coli*", The EMBO Journal, vol. 3, No. 10, 1984, pp. 2437-2442.

Marc Better, et al., "*Escherichia coli* Secretion of an Active Chimeric Antibody Fragment", Science, vol. 240, 1988, pp. 1041-1043.

Dana L. Johnson, et al., "Refolding, Purification, and Characterization of Human Erythropoietin Binding Protein Produced in *Escherichia coli*", Protein Expression and Purification, vol. 7, Article No. 0014, 1996, pp. 104-113.

Charles S. Hoffman, et al., "Fusions of secreted proteins to alkaline phosphatase: An approach for studying protein secretion", Proc. Natl. Acad. Sci. USA, vol. 82, Aug. 1985, pp. 5107-5111.

Lydia Villa-Komaroff, et al "A bacterial clone synthesizing proinsulin", Proc. Natl. Acad. Sci. USA, vol. 75, No. 8, Aug. 1978, pp. 3727-3731.

Li Ming Shen, et al., "Use of Site-Directed Mutagenesis to Define the Limits of Sequence Variation Tolerated for Processing of the M13 Procoat Protein by the *Escherichia coli* Leader Peptidase", Biochemistry, vol. 30, 1991, pp. 11775-11781.

John W. Puziss, et al., "Analysis of Mutational Alterations in the Hydrophilic Segment of the Maltose-Binding Protein Signal Peptide", Journal of Bacteriology, vol. 171, No. 5, May 1989, pp. 2303-2311.

Hiroshi Oneda, et al., "Refolding and Recovery of Recombinant Human Matrix Metalloproteinase 7 (Matrilysin)from Inclusion Bodies Expressed by *Escherichia coli*[1]", J. Biochem. vol. 126, No. 5, 1999, pp. 905-911.

Thomas Crabbe, et al., "Biochemical Characterization of Matrilysin. Activation Conforms to the Stepwise Mechanisms Proposed for Other Matrix Metalloproteinases", Biochemistry, vol. 31, No. 36, 1992, pp. 8500-8507.

Halfmann, G. et al. "Targeting of interleukin-2 to the periplasm of *Escherichia coli*." Journal of General Microbiology, vol. 139. pp. 2465-2473 (1993).

International Search Report issued Nov. 24, 2009 in PCT/JP09/68133 filed Oct. 21, 2009.

* cited by examiner

PROCESS FOR PREPARING INCLUSION BODY-FORMING PROTEIN

TECHNICAL FIELD

The present invention relates to a process for preparing a protein that forms an inclusion body when expressed in prokaryotic cells (hereinafter also referred to as "inclusion body-forming protein") and a nucleic acid fragment for use in said process. More particularly, the present invention relates to a process for preparing an inclusion body-forming protein comprising steps of: (1) preparing an expression vector that contains a nucleic acid fragment incorporated therein consisting of a nucleotide sequence coding for a modified signal peptide with a nucleotide sequence coding for a protein of interest bound downstream thereof, (2) preparing a host cell transformed with said expression vector that produces an inclusion body-forming protein and (3) purifying the inclusion body-forming protein from culture obtained by culturing the host cell that produces the inclusion body-forming protein, and the nucleic acid fragment in (1) above.

A protein of interest may most preferably be matrix metalloprotease 7 (hereinafter also referred to as "MMP-7"). Therefore, the most preferable embodiment of the present invention relates to a nucleic acid fragment comprising a nucleotide sequence coding for a modified signal peptide and a nucleotide sequence coding for pro-matrix metalloprotease 7 (hereinafter also referred to as "proMMP-7", and a process for preparing MMP-7 by using said nucleic acid fragment.

BACKGROUND ART

When a protein is produced in Gram-negative bacteria such as *E. coli*, a protein of interest may often be secreted into a space called periplasm between the inner membrane (the cell membrane) and the cell wall by attaching a signal sequence at the N-terminal of said protein. However, efficiency of transmitting a protein of interest into periplasm through the inner membrane varies depending on a combination of a signal sequence and a protein of interest and there is no known approach for affording always high transmission. It is known that a proteolytic enzyme (protease) is also secreted into periplasm of *E. coli* and thus a protein of interest secreted into periplasm may be subject to proteolysis.

On the other hand, when a protein of interest is secreted into periplasm under denaturation condition, the protein may sometimes form a structure called an inclusion body. It is said that a protein of interest incorporated into an inclusion body is not likely to be subject to proteolysis by protease. Besides, since an inclusion body incorporates a high concentration of a protein of interest, it may advantageously be used in view of efficiency of purification and high-yield recovery. However, there is no known approach at present for expressing a protein of interest in Gram-negative bacteria such as *E. coli* and forming efficiently an inclusion body by e.g. modifying a signal peptide.

Ibrahim et al. showed that, by substituting leucine with proline at P8 in a hydrophobic core region of a signal in endotoxin subunit B of *E. coli* in cell-free protein synthesizing system using wheat germ, cleavage of a signal sequence is prohibited and a synthetic rate increased two-fold (cf. e.g. Non-patent reference 1). However, since the results of this process are outcome of a simplified expression system with cell-free system, the process would not necessarily be applicable to an expression system with living cells such as *E. coli*. In addition, a protein synthesized by this process was soluble and did not form an inclusion body.

There is another report that, when mutation (mutation from leucine to proline at P17) occurs spontaneously in a signal sequence of a ribose-binding protein in *E. coli*, cleavage of a signal sequence is prohibited and a soluble ribose-binding protein precursor is accumulated in cytoplasm, and that its expression level was so small that detection with labeling using radioisotope was necessary and was equivalent to that of a wild-type protein before mutation (cf. e.g. Non-patent reference 2). As such, an effect of mutation in a signal sequence from prokaryotic cells on expression of an inclusion body in *E. coli* has not well been elucidated and, in particular, an effect of the mutation on expression of a structural gene from eukaryotic cells is utterly not known.

When a recombinant cell with a heterologous gene incorporated therein is used for production of a protein, if a selection medium containing antibiotics is not used, it may occur that a recombinant cell excludes the incorporated gene during proliferation to lose the character of said gene and such a recombinant cell may predominantly proliferate to result in reduced efficiency in production of a protein. Thus, when a gene (e.g. an expression plasmid) is introduced into a host cell, such a gene that affords resistance to antibiotics used for selection through degradation or modification of the antibiotics is also simultaneously introduced into the host cell and cell culture is performed in a selection medium containing antibiotics toxic to a host cell not conveying said gene (such as e.g. ampicillin and tetracycline) to allow for selection of those recombinant cells that carry the gene and for restraint of generation of those recombinant cells that exclude the introduced gene.

However, antibiotics may be toxic to living organisms and cause drug hypersensitivity (allergy). Accordingly, for the manufacture and sale of a medicament, an animal drug or a food stuff using a recombinant cell, their contamination with antibiotics needs strictly be controlled. As such, a constitution and a method are desired where an introduced gene may be maintained without selection with antibiotics.

MMP-7 is among matrix metalloproteases (hereinafter also referred to as "MMP") belonging to a zinc-type metalloprotease family where a zinc molecule is present at the active site (cf. e.g. Non-patent reference 3). MMP is produced as a precursor. The precursor is processed to cleave a signal sequence when extracellularly secreted and then processed to cleave a pro sequence to generate an active form. It is reported that extracellularly secreted MMP is involved in metabolism of extracellular matrix whereas MMP-7 is mainly secreted from cancer cells and is involved in infiltration and metastasis of cancer (cf. e.g. Non-patent reference 4). MMP-7, not possessing a hinge domain and a hemopexin-like domain unlike other MMPs, consists of the minimum molecular unit among MMP and its substrate is collagen and components that constitute extracellular matrix such as fibronectin, vitronectin, laminin and aggrecan.

It is assumed that MMP-7 may be involved in natural resorption on of hernia disk viewing that its substrate is aggrecan, a principal component of cartilage, and that macrophages from samples from surgical operation of disk herniation express MMP-7 (cf. e.g. Non-patent reference 5). Subsequently, Haro et al. observed reduction in a volume of the nucleus pulposus in the intervertebral disks after administration of MMP-7 into the intervertebral disks of hernial dogs and showed possible use of MMP-7 as a medicament for disk herniation (cf. e.g. Non-patent reference 6). Development of MMP-7 for medical usage is desired. However, MMP-7 occurs only in a trace amount in the living body and thus its isolation and purification from the living body is extremely difficult. Besides, when living material is used, there will be concern for safety problem such as potential viral contamination. Although MMP-7 may be obtained from cancer cells, it is not preferable to use cancer cells as a source for production (cf. e.g. Non-patent reference 7).

For solving the above problems, an attempt to obtain MMP-7 by a genetic recombination technique has been made. For a system using animal cells, there is a report by Barnett et al. that MMP-7 is expressed in CHO cells (cf. e.g. Non-patent reference 8). However, an expression level of MMP-7 is as low as around several mg/L and thus the reported system is not actually suited for production of a medicament. It is also reported that a nucleic acid fragment in which a nucleotide sequence coding for a signal sequence of alkali phosphatase and a gene sequence of proMMP-7 with optimization to codon usage in E. coli are bound to each other is used to allow for expression of soluble MMP-7 at 34° C. and expression of insoluble MMP-7 at 42° C. (cf. e.g. Patent reference 1).

PRIOR ART DOCUMENTS

Patent reference 1: Japan Patent No. 293852
Non-patent reference 1: Ibrahim et al., J. Biol. Chem., 1987, vol. 262, p. 10189-10194
Non-patent reference 2: Groarke et al., EMBO J., 1985, vol. 4, p. 1875-1880
Non-patent reference 3: Soler et al., Biochem Biophys Res Commun, 1994, vol. 201, p. 917-923
Non-patent reference 4: Ii et al., Exp Biol Med (Maywood), 2006, vol. 231, p. 20-27
Non-patent reference 5: Haro et al., J. Spinal Disord, 1999, vol. 13, p. 245-249
Non-patent reference 6: Haro et al., J Orthop Res, 2005, vol. 23, p. 412-419
Non-patent reference 7: Miyazaki et al., Cancer Research, 1990, vol. 50, p. 7758-7764
Non-patent reference 8: Barnett et al., Protein Exp. Purif., 1994, vol. 5, p. 27-36

DISCLOSURE OF THE INVENTION

Technical Problem to be Solved by the Invention

As described above, when proMMP-7 gene is introduced into E. coli, proMMP-7 is not expressed due to its strong toxicity to E. coli. Attaching a signal peptide at the N-terminal of proMMP-7 allows for its expression in E. coli. However, with mere addition of a signal peptide, an expression level of proMMP-7 is low and a portion of expressed proMMP-7 may undergo proteolysis by a protease. The proteolysis, as bringing about reduction in expression product in E. coli or reduction in yield in refolding from an inclusion body, may hamper establishment of a process for preparing proMMP-7 efficiently.

Accordingly, an object of the present invention is to provide a novel combination of gene fragments that allows for increase in an expression level and inhibition of proteolysis by a protease, a method for expressing a protein of interest in prokaryotic cells using said combination of gene fragments, and a process for preparing a protein of interest.

Means for Solving the Problems

The present inventors have assiduously investigated in order to attain the objects as described above, and as a result, have found that: (1) expression in E. coli of a nucleic acid fragment comprising a nucleotide sequence coding for a modified PhoA-alkaline phosphatase signal peptide (hereinafter also referred to as "modified APSP") attached to the 5'-end of proMMP-7 inhibited degradation of proMMP-7 by a protease, wherein said modified APSP is obtained by substituting alanine at the 21st position, which is a signal peptidase-binding site, in the amino acid sequence of PhoA-alkaline phosphatase signal peptide (hereinafter also referred to as "APSP") shown by SEQ ID NO: 1 with an arbitrary amino acid, e.g. aspartic acid, glutamic acid, lysine, histidine, phenylalanine or tyrosine; (2) the use of a modified APSP where leucine at the 13th position is substituted with proline provided both an increased expression level of proMMP-7 and inhibition of degradation of proMMP-7 by a protease; and (3) the use of a modified APSP where leucine at the 13th position is substituted with proline and alanine at the 21st position is substituted with an arbitrary amino acid as described above provided an increased expression level of proMMP-7 as compared to a modified APSP where either of the amino acid at the 13th position or at the 21st position is substituted in induction of expression with isopropylthio-beta-D-galactoside (IPTG). Furthermore, the present inventors have found that the modified signal peptide as described above may exert the same effect with other inclusion body-forming protein such as e.g. HMTp210 of type C *Avibacterium paragarinarum* to thereby complete the present invention.

Thus, the present invention includes the followings:

[1] A nucleic acid fragment consisting of a nucleotide sequence coding for a protein that forms an inclusion body when expressed in prokaryotic cells (inclusion body-forming protein), said fragment comprising a nucleotide sequence coding for a modified signal peptide and a nucleotide sequence coding for a protein of interest.

[2] The nucleic acid fragment of [1] as above wherein said prokaryotic cells are Gram negative bacteria.

[3] The nucleic acid fragment of [1] or [2] as above wherein said prokaryotic cells are E. coli.

[4] The nucleic acid fragment of any one of [1] to [3] as above wherein said protein of interest is pro-matrix metalloprotease 7 (proMMP-7) or HMTp210 of type C Avibacterium paragarinarum.

[5] The nucleic acid fragment of any one of [1] to [4] as above wherein said modified signal peptide is a signal peptide with modification of a protein from prokaryotes that penetrates the inner membrane.

[6] The nucleic acid fragment of [5] as above wherein said protein is selected from the group consisting of alkaline phosphatase, OmpA, PelB, OmpT, LamB, OmpF and β-lactamase.

[7] The nucleic acid fragment of [5] as above wherein said modified signal peptide is a signal peptide with modification of PhoA-alkaline phosphatase (modified APSP).

[8] The nucleic acid fragment of [7] as above wherein said modified APSP has the amino acid sequence of SEQ ID NO: 1 with substitution of leucine at the 13th position with any one of the amino acids selected from the group consisting of proline, phenylalanine and tryptophan.

[9] The nucleic acid fragment of [7] as above wherein said modified APSP has the amino acid sequence of SEQ ID NO: 1 with substitution of alanine at the 21st position with any one of the amino acids selected from the group consisting of aspartic acid, glutamic acid, lysine, histidine, phenylalanine and tyrosine.

[10] The nucleic acid fragment of [7] as above wherein said modified APSP has the amino acid sequence of SEQ ID NO: 1 with substitution of leucine at the 13th position with any one of the amino acids selected from the group consisting of proline, phenylalanine and tryptophan and with substitution of alanine at the 21st position with any one of the amino acids selected from the group consisting of aspartic acid, glutamic acid, lysine, histidine, phenylalanine and tyrosine.

[11] The nucleic acid fragment of any one of [1] to [10] as above wherein a nucleotide sequence coding for a protein of interest is placed downstream of the nucleotide sequence coding for the modified signal peptide.

[12] An expression vector in which the nucleic acid fragment of any one of [1] to [11] as above is incorporated.

[13] A host producing an inclusion body-forming protein obtained by transforming a host with the expression vector as set forth in [12] as above.

[14] The host producing an inclusion body-forming protein of [13] as above wherein the host is prokaryotic cells.

[15] The host producing an inclusion body-forming protein of [13] or [14] as above wherein the host is Gram negative bacteria.

[16] The host producing an inclusion body-forming protein of any one of [13] to [15] as above wherein the host is E. coli.

[17] A process for preparing a protein that forms an inclusion body when expressed in prokaryotic cells (an inclusion body-forming protein) consisting of the following steps (1) to (3):

(1) preparing an expression vector that contains the nucleic acid fragment of any one of [1] to [11] as above incorporated therein, (2) preparing a host cell transformed with the expression vector of step (1) above that produces an inclusion body-forming protein, and (3) purifying the inclusion body-forming protein from culture obtained by culturing the host cell of step (2) above that produces the inclusion body-forming protein.

[18] The process of [17] as above wherein said expression vector is an expression vector where the nucleic acid fragment of any one of [1] to [11] as above is incorporated downstream of T7 promoter.

[19] The process of [17] or [18] as above wherein the host is prokaryotic cells.

[20] The process of any one of [17] to [19] as above wherein the host is Gram negative bacteria.

[21] The process of any one of [17] to [20] as above wherein the host is E. coli.

[22] The process of any one of [17] to [21] as above wherein the host cell that produces the inclusion body-forming protein is cultured in an antibiotic-free culture medium.

Effects of the Invention

In accordance with the present invention, provided are a nucleic acid fragment consisting of a nucleotide sequence coding for a protein that forms an inclusion body when expressed in prokaryotic cells (inclusion body-forming protein), said fragment consisting of a nucleotide sequence coding for a modified signal peptide and a nucleotide sequence coding for a protein of interest, an expression vector in which said nucleic acid fragment is incorporated, a host producing an inclusion body-forming protein transformed with said expression vector, and a process for preparing an inclusion body-forming protein using said host producing an inclusion body-forming protein.

By using the process of the present invention, a ratio of retaining an expression plasmid may be improved to thereby make it unnecessary to add an antibiotic such as ampicillin, as used for retaining a plasmid, to a culture medium. Also, in accordance with the present invention, better responsiveness in a variety of induction systems for expression of a protein of interest may be obtained and an expression level of a protein of interest may be improved. Besides, in accordance with the present invention, degradation by a protease of a protein of interest incorporated into an inclusion body may be decreased and refolding efficiency may be improved to thereby ultimately allow for increase in efficiency of recovery of a functionally active protein of interest. Thus, the process of the present invention allows for the manufacture of a protein of interest more easily.

For instance, by using a nucleic acid fragment comprising a nucleotide sequence coding for a modified APSP, downstream of which a nucleotide sequence of a gene of pro-matrix metalloprotease 7 (proMMP-7) is bound, an expression level of proMMP-7 in proMMP-7-producing E. coli may be increased and degradation of proMMP-7 by a protease from E. coli may be inhibited during the culture of said proMMP-7-producing E. coli and purification from said culture. Accordingly, in accordance with the process of the present invention, for instance, purification of proMMP-7 and conversion of proMMP-7 into MMP-7 may be facilitated to thereby allow for efficient production of MMP-7.

BEST MODE FOR CARRYING OUT THE INVENTION

Figure 1:
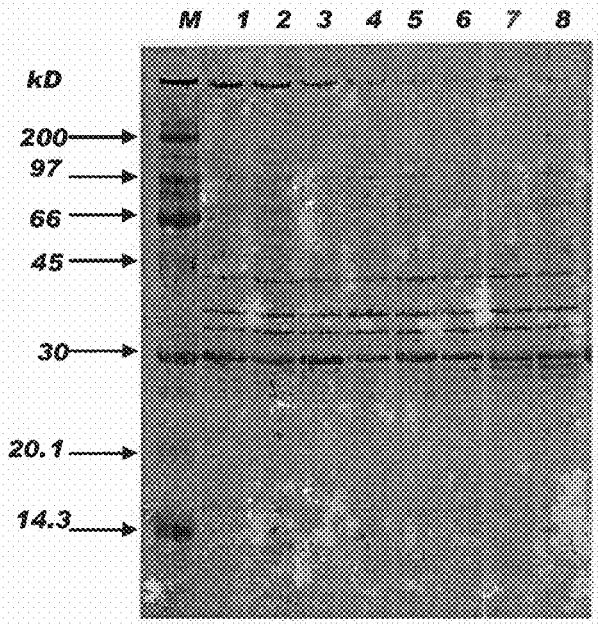
FIG. 1 shows results of SDS-PAGE, and subsequent CBB staining, with solubilized proMMP-7-producing E. coli obtained by transformation with an expression vector containing a modified APSP where the signal peptidase-binding site, i.e. Ala at the 21st position in the amino acid sequence shown by SEQ ID NO: 1, alone is substituted with the other amino acid. Lane 1: MMP7A21D strain, Lane 2: MMP7A21D strain, Lane 3: MMP7A21E strain, Lane 4: MMP7A21E strain, Lane 5: MMP7A21K strain, Lane 6: MMP7A21K strain, Lane 7: MMP7 strain, Lane 8: MMP7 strain

The present invention is characterized by that a host producing an inclusion body-forming protein is prepared by using a nucleic acid fragment which comprises a nucleotide sequence coding for a modified signal peptide, downstream of which a nucleotide sequence coding for a protein of interest is bound, and an inclusion body-forming protein or a protein of interest is prepared from the culture of said host producing an inclusion body-forming protein.

A modified signal peptide may be a signal peptide from any protein insofar that it can transfer a protein of interest from within cells into a periplasm or to the outside of cells via passing through membranes in an expression system using E. coli. Any signal peptide from the cytoplasm may be a candidate peptide, including, in particular, a signal peptide from a protein from prokaryotes that may pass through the inner membrane such as e.g. alkaline phosphatase (DA et al., Nature, vol. 321, 706-708), PhoA-alkaline phosphatase (Oka et al., 1985, Proc. Natl. Acad. Sci. USA, vol. 82, 7212-7216), OmpA (Ghrayeb et al., 1984, EMBO J., vol. 3, 2437-2442), PelB (Better et al., 1988, Science, vol. 240, 1041-1043), OmpT (Johnson et al., 1990, Protein Expression Purif, vol. 7, 104-113), LamB and OmpF (Hoffman et al., 1985, Proc. Natl. Acad. Sci. USA, vol. 82, 5107-5111), β-lactamase (Villa-komaroff et al., 1978, Proc. Natl. Acad. Sci. USA., vol. 75, 3727-3731), and the like. Preferably, a signal peptide of alkaline phosphatase may be used and, more preferably, a signal peptide of PhoA-alkaline phosphatase may be used. There are various isozymes in alkaline phosphatase from prokaryotic cells and a signal peptide from any isozymes may be used.

The process of the present invention may be used for an inclusion body-forming protein from eukaryotic cells. In particular, the process of the present invention may effectively be used in case that direct expression of a protein of interest may be toxic to prokaryotic cells or to thereby decrease cell growth or an expression level of the protein of interest or incase that a protein of interest may undergo degradation to result in decrease in a production level of the protein. Such a protein of interest includes proMMP-7, HMTp210 of type C *Avibacterium paragarinarum*, HIV-1 protease, T-cell receptor, antibacterial peptide, human apoptosis regulating protein BOX, and the like. A gene sequence of these proteins of interest may be as original or may be optimized for codon usage in E. coli. Hereinafter explained are embodiments of an inclusion body-forming protein which comprises a modified APSP downstream of which proMMP-7 is bound.

A gene coding for proMMP-7 may be obtained by performing PCR with a commercially available kidney-derived cDNA library (HumanMTC Panel I, Catalog number:K1420-1, BD). Primers for use in PCR may be designed based on the nucleotide sequence of proMMP-7 as disclosed in database Accession Numbers; NM002423;proMMP-7. Primers for use in PCR may readily be available if asked to DNA synthesis contractor (e.g. QIAGEN). When designed, nucleotide sequences of appropriate restriction enzyme recognition sites may be added at the 5'-end and the 3'-end as occasion demands. In Examples hereinbelow, primers consisting of the nucleotide sequences P1 (SEQ ID NO: 2) and P2 (SEQ ID NO: 3) where restriction enzyme recognition sites for NdeI and BamHI were added were used. A nucleic acid fragment amplified by PCR may be cloned into a cloning vector such as pCRII-TOPO (Invitrogen) and sequenced with a DNA sequencer (ABI Prism 377 Applied Biosystems). The obtained proMMP-7 gene may be confirmed by comparing the obtained nucleotide sequence with the known nucleotide sequence of proMMP-7. Thus, a nucleic acid fragment coding for proMMP-7 (hereinafter also referred to as "proMMP-7 gene") may be obtained. A nucleotide sequence coding for a human proMMP-7 is shown in SEQ ID NO: 21 whereas an amino acid sequence coding for a human MMP-7 is shown in SEQ ID NO: 22.

Next, PCR using the proMMP-7 gene as a template may be performed so as to add APSP or a modified APSP at the 5'-end of the proMMP-7 gene. For introducing mutation in an amino acid sequence for the production of a modified APSP, site-directed mutagenesis may be used. In practice, site-directed mutagenesis may be performed with commercially available kits in which this technique is applied, such as GeneTailor Site-Directed Mutagenesis System by Invitrogen, Site-Directed Mutagenesis System (Mutan-Super Express Km, Mutan-Express Km, Mutan-K, and the like) by Takara, QuickChange Multi Site-Directed Mutagenesis Kit, QuickChange XL Site-Directed Mutagenesis Kit, and the like by Stratagene, in accordance with protocol attached thereto. In Examples, GeneTailor Site-Directed Mutagenesis System was used.

It is known that a signal peptidase from E. coli recognizes P3-P1 site where a signal sequence is well conserved and mutation at this site renders cleavage of a signal peptide not occur (Shen et al., Biochemistry, 1991, vol. 30, 11775-11781). It is known that a typical signal peptide has a hydrophobic core region where an amino acid residue with a side chain of hydrophobic property occurrs at a relatively high frequency. It is also possible to inhibit the function of a signal peptide by mutating an amino acid in a signal sequence into an amino acid of different polarity (PUZISS et al., J. Bacteriol., 1989, 2303-2311).

Mutation may be introduced at any site in APSP insofar that degradation of proMMP-7 by a protease may be inhibited. Preferably, mutation may be introduced at a signal peptidase-binding site, more preferably, at Ala at the 21st position. Mutation to be introduced may be any of substitution, deletion or addition of an amino acid. Preferably, Ala at the 21st position may be substituted with the other amino acid, preferably, with an amino acid selected from the group consisting of aspartic acid, glutamic acid, lysine, histidine, phenylalanine and tyrosine.

Besides, amino acid substitution that results in change in steric structure of APSP may be used to allow for increase in an expression level of proMMP-7 (acceleration of translation as a fusion protein and increase in a ratio of retaining a plasmid) and inhibition of degradation by a protease simultaneously. An amino acid likely to induce change in steric structure includes proline, phenylalanine, tryptophan, and the like, preferably, proline. Substitution site for such an amino acid may be anywhere at other amino acid than proline, preferably at leucine at the 13th position.

Moreover, when a modified APSP where leucine at the 13th position is substituted with proline and alanine at the 21st position is substituted with any of the amino acids as described above is bound at the N-terminal of proMMP-7, an increased expression level in expression induction with IPTG may be obtained as compared to each alone of the two substitutions. Thus, the most preferable embodiment of a modified APSP is a modified APSP where both substitution of leucine at the 13th position with proline and substitution of alanine at the 21st position with any of the amino acids as described above are introduced. As described above, phenylalanine or tryptophan may be used instead of proline.

Depending on its origin, APSP has an amino acid sequence with one or more amino acids added either to the N-terminal of the amino acid sequence of APSP as shown in SEQ ID NO: 1 or to the N-terminal of the above sequence but with the N-terminal methionine removed. Such APSP may also be used as a modified APSP of the present invention by conducting modification of substitution as described above at an amino acid corresponding to leucine at the 13th position and/or alanine at the 21st position in SEQ ID NO: 1. Examples of such APSP from different species include those from *E. coli* UTI89 strain (Acc. No. YP 539434), *E. coli* CFT073 strain (Acc. No. NP 752424), and Shigella flexneri 2a Str301 (Acc. No. NP 706185). APSP from different species described herein consists of an amino acid sequence (SEQ ID NO: 20) where a sequence corresponding to No. 2 to No. 21 in SEQ ID NO: 1 of APSP is retained and 24 amino acid residues are added at the N-terminal thereof. Any APSP from different species may be used insofar that it may act as APSP.

The proMMP-7 gene added with the thus obtained APSP or the modified APSP where various amino acid substitutions are introduced may be incorporated into an appropriate expression vector and a host cell may be transformed with said expression vector for expression of proMMP-7. Since APSP from prokaryotic cells is used in the present invention, *E. coli* may preferably be used as a host cell. When *E. coli* is used as a host cell, various expression vectors having trp promoter, T7 promoter, cspA promoter, and the like for expression in *E. coli* have been developed and commercially available and may be used as appropriate. Depending on an expression vector, suitable *E. coli* such as BL21, HMS174, DH5 α, HB101, JM109, and the like may be selected as a host. Transformation of *E. coli* may be conducted using commercially available competent cells in accordance with protocol attached thereto. Thus, recombinant *E. coli* producing the desired polypeptide may be obtained. For culture medium (e.g. LB, SOC, SOB, and the like) used for culture of *E. coli*, reagents used for selection of transformant (e.g. ampicillin) and reagents used for expression induction (e.g. indole acetic acid (IAA), isopropylthio-β-D-galactoside (IPTG), and the like), commercially available ones may be used. A pH of a culture medium may be within a range suitable for growth of *E. coli* (pH 7.2 to 7.6).

For transformation of a host cell, methods known in the art may be used. For instance, calcium phosphate, DEAE dextran, approach using liposome of lipofectin, polyethylene glycol fusion of protoplast, electroporation, and the like may be used, as appropriately selected depending on a host cell as used. In Examples described hereinbelow, pET22b (Merck, manufacture code: 69744-3) for an expression vector, BL21 (DE3) for a host cell, and Overnight Express Autoinduction System 1 (Merck, manufacture code: 71300-3), where expression is induced with lactose, for an expression system were used for expression of proMMP-7.

Screening of recombinant *E. coli* expressing proMMP-7 may be carried out as described below. Cells cultured and grown in the presence of an expression inducer (Overnight Express Autoinduction System 1 was used in an expression system in the present invention) are measured for their turbidity (OD600 nm) and culture with a fixed amount of cells is subject to high-speed centrifuge to collect the cells. The cells are suspended in a fixed volume of distilled water, disrupted by sonication or a homogenizer such as French press or Manton Golin and subject to high-speed centrifuge (15,000 rpm, 15 minutes) for recovery in precipitate. To distilled water may appropriately be added a surfactant (e.g. Triton X 100, BugBuster (Merck)), a chelating agent (e.g. EDTA), lysozyme, and the like. proMMP-7 (forming an inclusion body) recovered in precipitate may be solubilized with Sample Buffer for SDS-PAGE, and a fixed amount thereof may be subject to SDS-polyacrylamide gel electrophoresis, and after staining with Coomassie Brilliant Blue, expression and an extent of expression of proMMP-7 protein may be confirmed by a molecular size and stained image. For confirmation (or detection) of proMMP-7, approach based on an antigen-antibody reaction such as ELISA, Western blot, dot blot, and the like may also be used other than approach based on a molecular size as described above. All of these approaches are commonly used for detecting a heterologous protein or polypeptide expressed in *E. coli* and may be selected as appropriate.

Recovery of MMP-7 from the thus obtained proMMP-7-producing *E. coli* may be carried out as described below. First, the proMMP-7-producing *E. coli* may be cultured and the proliferated cells may be disrupted by an appropriate procedure to thereby let an inclusion body consisting of proMMP-7 be released out of the cells. In the conventional gene recombination technique using *E. coli*, a resistant gene to an antibiotic such as ampicillin has been used as a selective marker gene for selection of a gene recombinant. However, the use of an antibiotic is obstruct for the development of technique of industrial production in view of its expansion to environment or concern for safety of a medical product. Also, for the manufacture and sale of a medicament or a medicament for animals using a gene recombinant, strict management would be necessary for avoiding its contamination. With these backgrounds, for a culture medium for industrial production, a antibiotic-free medium may preferably be used with sufficient consideration to safety. For disruption of cells, any conventional procedures may be employed including dissolution with a chemical substance, a surfactant, an enzyme, and the like or physical treatment such as French press or sonication. By combining several of these procedures, cells may be disrupted more effectively. Repetition of centrifuge and washing of a solution of the disrupted cells containing an inclusion body may remove most of cell debris. Washing may be carried out with a common buffer such as Tris buffer, phosphate buffer, glycine buffer, carbonate buffer, and the like. An inclusion body may be recovered by centrifuge of a solution containing an inclusion body as a precipitate.

The recovered inclusion body may be dissolved in a solution containing a reducing agent and a degenerating agent. For such a reducing agent, cysteine, glutathione, dithiothreitol, 2-mercaptoethanol, and the like may be used. Several of these may be used in combination. A concentration of a reducing agent may be in a range of 10 to 200 mM depending on an amount of an inclusion body to be dissolved. For a degenerating agent, urea, guanidine hydrochloride, and the like may be used. Urea and guanidine hydrochloride may be used at a concentration ranging from 4 to 8 M and from 2 to 6 M, respectively. A buffer may be those used for recovery of an inclusion body. A temperature when dissolved may not particularly be limited provided that it is 40° C. or less. Time for dissolution may be set while observing an extent of dissolution of an inclusion body and usually stirring may be continued for 30 minutes to 1 hour.

Next, a refolding buffer containing a surfactant and a metallic ion may be added to a solution of an inclusion body so as to perform refolding, i.e. construction of normal steric structure, of proMMP-7. Brij 35 for a surfactant and zinc acetate or cobalt chloride for a metallic ion as used thereby may be employed at a concentration ranging from 0.5 to 2% and from 0.05 mM to 0.2 mM, respectively. A kind and a concentration of a buffer for use in refolding may be the same as those used for dissolving an inclusion body. A buffer may be used at pH ranging from 7.0 to 9.0. Refolding may be performed by letting the solution left to stand for a day or more.

For purifying proMMP-7 from the refolding solution, a combination of the methods commonly used in the field of protein chemistry may be used such as e.g. centrifuge, salting-out, ultrafiltration, isoelectric focusing, electrophoresis, ion exchange chromatography, gel filtration chromatography, affinity chromatography, hydrophobic chromatography, hydroxyapatite chromatography, and the like. An amount of the obtained protein or polypeptide may be measured with a reagent for protein measurement such as BCA Protein Assay Reagent Kit (Pierce Biotechnology, Inc), Protein Assay Kit (BIO-RAD, Inc), and the like. For instance, proMMP-7 may be purified by having proMMP-7 be adsorbed to a cation column, and after washing, eluting proMMP-7 at a high salt concentration (Oneda et al., J. Biochem., 1999, vol. 126, 905-911).

Next, conversion of proMMP-7 into MMP-7 may be performed. For conversion, a solution containing proMMP-7 may be either incubated in the presence of 1 mM (4-aminophenyl)mercuric acetate (APMA) or 0.2 μM trypsin at 37° C. or incubated at 53° C. (Crabbe et al., Biochemistry, 1992, vol. 31, 8500-8507). Incubation time may be in a range of from 1 to 48 hours but may suitably be adjusted depending on a concentration of the reagent as well as proMMP-7 and their amount to be treated. Trypsin may be used after treatment with N-tosyl-L-phenylalanine chloromethyl ketone (TPCK).

For the measurement of the activity of MMP-7, cleavage of a fluorescent substrate (Dnp-Pro-Leu-Gly-Leu-Trp-Ala-D-Arg-NH$_2$: SEQ ID NO: 23) by MMP-7 may be measured with a fluorometer (Crabbe et al., Biochemistry, 1992, vol. 31, 8500-8507). In practice, Kits for measuring the activity of MMP-7 in which this technique is applied is commercially available (ANASPEC) and may be used for measuring the activity in accordance with protocol attached thereto. For isolation and purification of the thus obtained MMP-7 from proMMP-7, the technique for purification of a protein as described above may be used.

For obtaining HMTp210 gene of type C *Avibacterium paragarinarum*, PCR may be performed using a total RNA, mRNA or genomic DNA extracted from the cells as a starting material. Primers for use in PCR may be designed based on the nucleotide sequence of the HMTp210 gene from HPG-C type bacterium disclosed by Tokunaga et al. (Japanese patent publication No. 10-514499). Cloning of HMTp210 gene, construction of an expression vector, expression and purification of HMTp210 protein may be carried out as in proMMP-7.

MMP-7 and HMTp210 obtained by the process of the present invention may be prescribed to a pharmaceutical formulation for therapy, diagnosis and other usages. For instance, MMP-7, for a formulation for intravenous administration, may be dissolved in an aqueous solution that usually contains a physiologically compatible substance such as e.g. sodium chloride or glycine and has a buffered pH compatible to physiological conditions. It may also be conceived that a final dosage form may be in a lyophilized preparation to ensure stability for a prolonged period of time. Guidelines for a composition administered intravenously have been established by governmental regulations such as e.g. "MINIMUM REQUIREMENTS FOR BIOLOGICAL PRODUCTS". Specific use of a pharmaceutical composition comprising as an active ingredient MMP-7 of the present invention includes e.g. therapy for administration to patients suffering from disk herniation.

The present invention is explained in more detail by means of the following Examples but is not construed to be limited thereto.

EXAMPLE 1

Construction of proMMP-7 Expression Vector (pETMMP7) having APSP proMMP-7 gene was amplified from kidney cDNA library (HumanMTC Panel I, Catalog#: K1420-1, BD) by PCR using primers P1 (SEQ ID NO: 2) and P2 (SEQ ID NO: 3). The amplified DNA was inserted into a cloning vector (pCRII-TOPO, Invitrogen) and the obtained DNA was sequenced. For nucleotide sequencing, a DNA sequencer was used. Homology search was conducted between said nucleotide sequence and the nucleotide sequence of proMMP-7 registered on database (Accession Numbers: NM002423) to obtain a plasmid (pCRproMMP-7) where proMMP-7 gene was inserted.

Next, using pCRproMMP-7 as a template, PCR was performed using primer P3 (SEQ ID NO: 4), which consists of a recognition sequence of restriction enzyme NdeI, a nucleotide sequence coding for PhoA-alkaline phosphatase signal peptide (APSP) sequence and a nucleotide sequence coding for the N-terminal of proMMP-7, and primer P4 (SEQ ID NO: 5), which consists of a recognition sequence of restriction enzyme BamHI and a nucleotide sequence coding for the C-terminal of proMMP-7. In the same manner as described above, the amplified DNA was inserted into a cloning vector and the obtained DNA was sequenced. After confirming that no mutation occurred in the nucleotide sequence, the obtained plasmid was cleaved with restriction enzymes NdeI and BamHI and inserted into an expression vector pET22b (Merck, manufacture code: 69744-3) which was previously cleaved with the same restriction enzymes to give a plasmid (pETMMP7) where proMMP-7 gene was inserted.

EXAMPLE 2

Construction of Expression Vector pETMMP7 having Modified APSP (1) Modification of Signal Peptidase Recognition Site Using GeneTailor Site-Directed Mutagenesis System (Invitrogen), mutation was introduced to a signal peptidase recognition site (alanine (Ala) at the 21st position in the amino acid sequence shown in SEQ ID NO: 1) of APSP in pETMMP7 obtained in Example 1. Mutation is introduced by performing PCR with a primer comprising the mutated sequence and a reverse primer comprising partly the same sequence as that of the primer using methylated pETMMP7 as a template. The targeted amino acid was substituted with aspartic acid (Asp), glutamic acid (Glu), or lysine (Lys), respectively.

(2) Modification Providing Structural Change in Signal Sequence

In the same manner as in (1) above, leucine (Leu) at the 13th position in APSP was substituted with proline (Pro).

(3) Modification of Signal Peptidase Recognition Site and Modification Providing Structural Change in Signal Sequence In the same manner as in (1) above, alanine at the 21st position was substituted with Asp, Glu, Lys, histidine (His), phenylalanine (Phe) or tyrosine (Tyr), and leucine at the 13th position in APSP was substituted with proline. Table 1 shows expression vectors having the respective modified APSP, what modification is made in APSP, and primers used for modification.

TABLE 1

| Expression vector | Modification in APSP | Primers used for modification | |
|---|---|---|---|
| | | 5'-Primer | 3'-Primer |
| pETMMP7 (A21D) | Ala at No. 21 to Asp | M1 (SEQ ID NO: 9) | P5 (SEQ ID NO: 6) |
| pETMMP7 (A21E) | Ala at No. 21 to Glu | M2 (SEQ ID NO: 10) | P5 (SEQ ID NO: 6) |
| pETMMP7 (A21K) | Ala at No. 21 to Lys | M3 (SEQ ID NO: 11) | P5 (SEQ ID NO: 6) |
| pETMMP7 (L13P) | Leu at No. 13 to Pro | M4 (SEQ ID NO: 12) | P7 (SEQ ID NO: 8) |
| pETMMP7 (L13P-A21D) | Ala at No. 21 to Asp Leu at No. 13 to Pro | M1 (SEQ ID NO: 9) | P6 (SEQ ID NO: 7) |
| pETMMP7 (L13P-A21E) | Ala at No. 21 to Glu Leu at No. 13 to Pro | M2 (SEQ ID NO: 10) | P6 (SEQ ID NO: 7) |
| pETMMP7 (L13P-A21K) | Ala at No. 21 to Lys Leu at No. 13 to Pro | M3 (SEQ ID NO: 11) | P6 (SEQ ID NO: 7) |
| pETMMP7 (L13P-A21H) | Ala at No. 21 to Glu Leu at No. 13 to Pro | M5 (SEQ ID NO: 13) | P6 (SEQ ID NO: 7) |
| pETMMP7 (L13P-A21F) | Ala at No. 21 to His Leu at No. 13 to Pro | M6 (SEQ ID NO: 14) | P6 (SEQ ID NO: 7) |
| pETMMP7 (L13P-A21Y) | Ala at No. 21 to Tyr Leu at No. 13 to Pro | M7 (SEQ ID NO: 15) | P6 (SEQ ID NO: 7) |

EXAMPLE 3

Expression of pETMMP7 having Non-Modified or Modified APSP pETMMP7 having non-modified APSP obtained in Example 1 and pETMMP7 having modified APSP obtained in Example 2 were used to transform *E. coli* (BL21(DE3)) for expression of proMMP-7. Table 2 shows expression vectors used for transformation and the obtained *E. coli* producing proMMP-7.

TABLE 2

| Expression vector | *E. coli* producing proMMP-7 |
|---|---|
| pETMMP7 | MMPI |
| pETMMP7 (A21D) | MMP7A21D |
| pETMMP7 (A21E) | MMP7A21E |
| pETMMP7 (A21K) | MMP7A21K |
| pETMMP7 (L13P) | MMP7L13P |
| pETMMP7 (L13P-A21D) | MMP7L13P-A21D |
| pETMMP7 (L13P-A21E) | MMP7L13P-A21E |
| pETMMP7 (L13P-A21K) | MMP7L13P-A21K |
| pETMMP7 (L13P-A21H) | MMP7L13P-A21H |
| pETMMP7 (L13P-A21F) | MMP7L13P-A21F |
| pETMMP7 (L13P-A21Y) | MMP7L13P-A21Y |

Induction of expression was performed using Overnight Express Autoinduction System 1 (Merck, manufacture code: 71300-3) in accordance with protocol attached thereto. Briefly, each colony was suspended in 50 mL LB medium containing 50 μg/mL Ampicillin (Wako Pure Chemical Industries, Ltd.) in 125 mL Conical flask and, after adding the reagent from the kit, incubated at 37° C. for 16 hours. The cell suspension was measured for OD600 nm and the cells corresponding to OD600 nm=20, 1 mL were collected by centrifuge as precipitate. The precipitate was disrupted with 200 μL BugBuster and, after centrifuge, precipitate was obtained. The precipitate was solubilized in Sample Buffer for SDS-polyacrylamide gel electrophoresis (SDS-PAGE), subject to 15% polyacrylamide gel SDS-PAGE and CBB stained. As a result, MMP7A21D, MMP7A21E and MMP7A21K cells, which were obtained by transformation with expression vectors having modified APSP where a signal peptidase-binding site (Ala at the 21st position) alone was substituted with the other amino acids, exhibited a decreased amount of degraded product (MW 28-30 kD) of proMMP-7 as compared to MMP7 cells, which were obtained by transformation with expression vectors having non-modified APSP (cf. FIG. 1).

Figure 2:
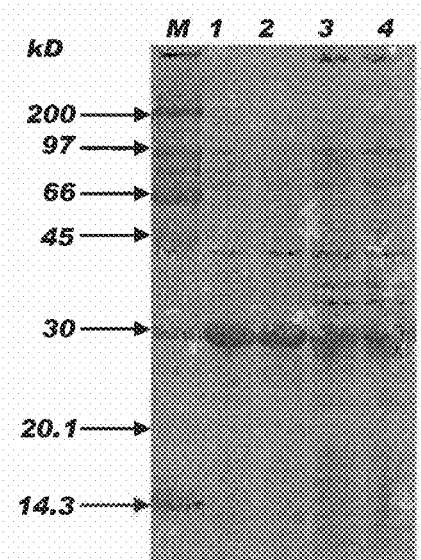
FIG. 2 shows results of SDS-PAGE, and subsequent CBB staining, with solubilized proMMP-7-producing E. coli obtained by transformation with an expression vector containing a modified APSP where Leu at the 13th position in the amino acid sequence shown by SEQ ID NO: 1 is substituted with Pro. Lane 1: MMP7L13P strain, Lane 2: MMP7L13P strain, Lane 3: MMP7 strain, Lane 4: MMP7 strain
Figure 3:
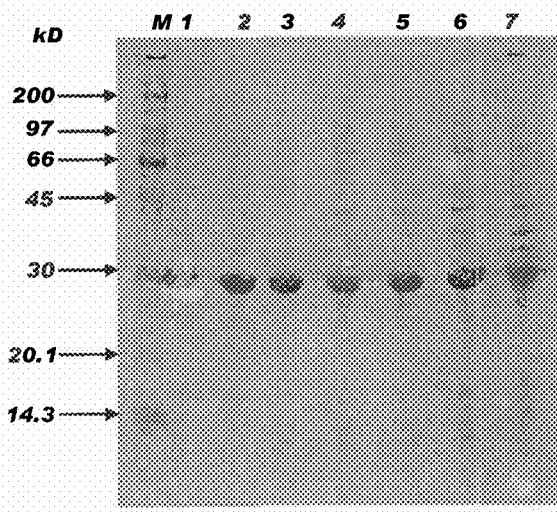
FIG. 3 shows results of SDS-PAGE, and subsequent CBB staining, with solubilized proMMP-7-producing E. coli obtained by transformation with an expression vector containing a modified APSP where Leu at the 13th position in the amino acid sequence shown by SEQ ID NO: 1 is substituted with Pro and Ala at the 21st position in the amino acid sequence shown by SEQ ID NO: 1 is substituted with the other amino acid. Lane 1: MMP7L13P-A21D strain, Lane 2: MMP7L13P-A21E strain, Lane 3: MMP7L13P-A21K strain, Lane 4: MMP7L13P-A21H strain, Lane 5: MMP7L13P-A21F strain, Lane 6: MMP7L13P-A21Y strain, Lane 7: MMP7 strain
Figure 4:
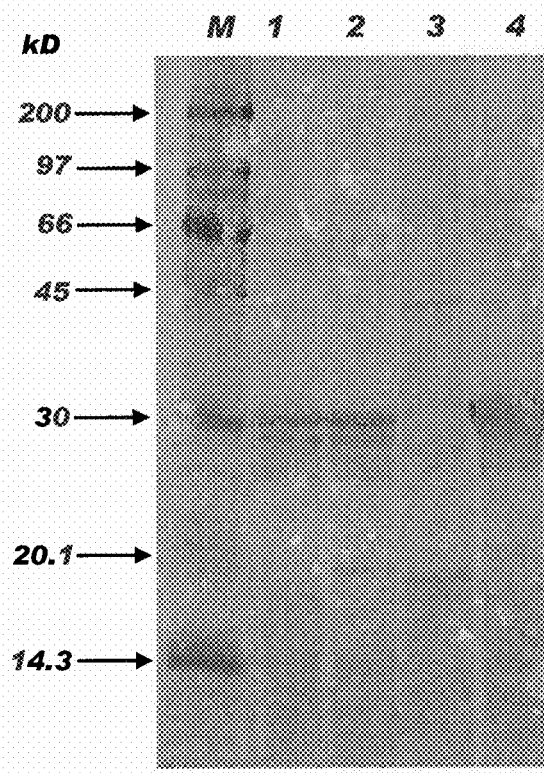
FIG. 4 shows results of SDS-PAGE, and subsequent CBB staining, with solubilized proMMP-7-producing E. coli obtained by transformation with an expression vector containing a modified APSP where Leu at the 13th position in the amino acid sequence shown by SEQ ID NO: 1 is substituted with Pro, where Ala at the 21st position in the amino acid sequence shown by SEQ ID NO: 1 is substituted with glutamic acid, and where these both modifications are made. Lane 1: MMP7 strain, Lane 2: MMP7L13P strain, Lane 3: MMP7A21E strain, Lane 4: MMP7L13P-A21E strain
Figure 5:
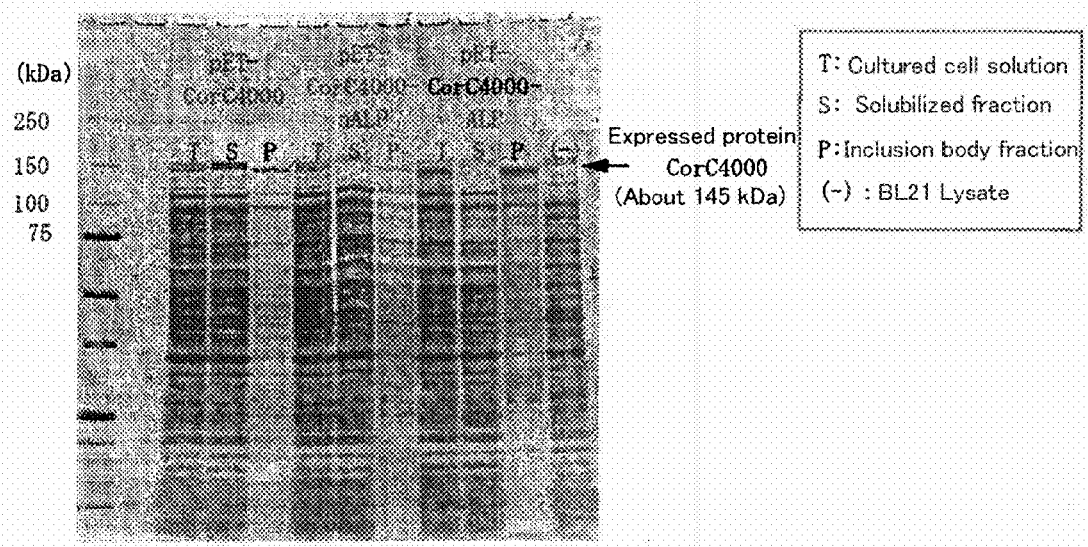
FIG. 5 shows results of SDS-PAGE, and subsequent CBB staining, with a portion of cell debris of E. coli BL21(DE3) in which either of an expression plasmid pET-CorC4000, pET-nALP-CorC4000, or pET-ALP-CorC4000 is introduced.

Besides, MMP7L13P cells, which were obtained by transformation with expression vector having modified APSP where Leu at the 13th position was substituted with Pro, exhibited increase in an expression level of proMMP-7 (MW kD) and inhibition of degradation as compared to MMP7 cells (cf. FIG. 2). Moreover, when MMP7L13P-A21D, MMP7L13P-A21E, MMP7L13P-A21K, MMP7L13P-A21H, MMP7L13P-A21F and MMP7L13P-A21Y cells, which were obtained by transformation with expression vectors having modified APSP where both Leu at the 13th position was substituted with Pro and Ala at the 21st position was substituted with the other amino acids, were subject to lactose induction (Overnight Express Autoinduction System 1), both effects of increase in an expression level and inhibition of degradation of proMMP-7 were enhanced (cf. FIG. 3). Also, when MMP7, MMP7L13P, MMP7A21E and MMP7L13P-A21E cells were subject to IPTG induction, increase in an expression level was observed in MMP7L13P-A21E (cf. FIG. 4).

EXAMPLE 4

Ratio of Retaining Plasmid in *E. coli* Producing proMMP-7

MMP7L13P-A21E and MMP7 cells obtained in Example 3 were suspended in 100 mL LB medium containing 50 μg/mL Ampicillin in 125 mL Conical flask and cultured for 6 hours and then the respective culture was inoculated to LB agar plate. Each 100 colonies were transferred to LB agar plate containing 50 μg/mL Ampicillin and growth of the colonies was observed. As a result, growth was observed in 100 colonies for MMP7L13P-A21E cells and in 28 colonies for MMP-7 cells.

MMP7L13P-A21E cells obtained in Example 3 were suspended in 100 mL Ampicillin-free LB medium and cultured for 6 hours and 10 μL of culture was subject to passage culture of the cells. The passage culture was repeated 6 times and then the culture was inoculated to LB agar plate. Each 100 colonies were transferred to LB agar plate containing 50 μg/mL Ampicillin and growth of the colonies was observed. As a result, growth was observed in 92 colonies.

EXAMPLE 5

Conversion from proMMP-7 into MMP-7

(1) Activation with Mercury

Using Overnight Express Autoinduction System 1, MMP7 and MMP7L13P-A21E cells underwent expression. The cells were disrupted with BugBuster and the precipitate was prepared. The precipitate was dissolved in an inclusion body-dissolving solution (6 M guanidine hydrochloride, 0.1 M DTT) at 10 µL per 1 mg of the precipitate. The solution dissolving an inclusion body was diluted 10-fold with a refolding buffer (0.1 mM zinc acetate, 0.2 M NaCl, 10 mM $CaCl_2$, 1% Brij 35/50 mM Tris-HCl, pH 7.5). proMMP-7 in the solution was activated with mercury in accordance with protocol of Kit for measuring MMP-7 activity (Enzolyte520MMP-7 Assay Kit, ANASPEC, manufacture code: 71153) and fluorescence of a cleaved fluorescent substrate was measured with a fluorometer. As a standard, proMMP-7 manufactured by Oriental Yeast Co. Ltd. was used. As a result, a concentration of proMMP-7 in the refolding solution was 36.2 µg/mL for MMP7 cells and 383.2 µg/mL for MMP7L13P-A21E cells, about 10-fold increase of the yield of proMMP-7 in the refolding solution.

(2) Autoactivation by Heating

The solution dissolving an inclusion body obtained in (1) above was diluted 100-fold with a refolding buffer (0.1 mM zinc acetate, 0.2 M NaCl 10 mM $CaCl_2$, 1% Brij 35/50 mM Tris-HCl pH 7.5). The refolding solution was incubated at 53° C. for 2 hours to carry out autoactivation of proMMP-7. To the solution was added a substrate from Kit for measuring MMP-7 activity without addition mercury and its fluorescence was measured with a fluorometer. As a standard, MMP-7 manufactured by Oriental Yeast Co. Ltd. was used. As a result, a concentration of MMP-7 in the incubating solution was 27 µg/mL for MMPI cells and 126 µg/mL for MMP7L13P-A21E cells.

EXAMPLE 6

Expression of HMTp210 of Type C *Avibacterium paragarinarum*

(1) Construction of Expression Vector for HMTp210 of Type C *Avibacterium paragarinarum*

A genomic DNA was extracted from type C *Avibacterium paragarinarum* 53-47 strain in accordance with the conventional procedures. Using S1 and S2 primers (SEQ ID NO: 16 and 17), 4000 by fragment (hereinafter referred to as "CorC4000") of HMTp210 gene, which is a gene of a protective antigen, was amplified by PCR. The PCR products were cleaved with restriction enzymes NcoI and XhoI and inserted into expression vector pET11d (Merck, manufacture code: 69439-3) which has previously been cleaved with the same restriction enzymes to give a plasmid (pET-CorC4000) in which the CorC4000 gene was inserted.

(2) Construction of HMTp210 Expression Vector having Modified APSP or Non-Modified APSP Using S3 and S4 primers (SEQ ID NO: 18 and 19), CorC4000 gene was amplified from pET-CorC4000 by PCR. The PCR products were cleaved with restriction enzyme BamHI and inserted into BamHI site of pET15b-ALP to give plasmid (pET-ALP-CorC4000) in which a nucleotide sequence coding for a modified APSP and the HMTp210 gene were inserted. Besides, the PCR products were cleaved with restriction enzyme BamHI and inserted into BamHI site of pET15b-nALP to give plasmid (pET-nALP-CorC4000) in which a nucleotide sequence coding for a non-modified APSP and the Knob-S134 gene were inserted.

(3) Expression of CorC4000

BL21(DE3) *E. coli* cells, in which the expression plasmid pET-CorC4000, pET-nALP-CorC4000 or pET-ALP-CorC4000 was introduced, were inoculated to 3 ml of Circle Grow (CG) medium containing 50 μg/ml of Ampicillin and cultured at 37° C. until turbidity at OD600nm reached 0.5 to 1.0. Then, after adding isopropylthio-β-D-galactopyranoside at a final concentration of 1 mM, the cells were cultured for further 16 hours to induce expression of CorC4000. The cultured *E. coli* cells were collected by centrifuge. The precipitate was disrupted with BugBuster and was subject to centrifuge to give precipitate. The precipitate was solubilized with Sample Buffer for SDS-polyacrylamide gel electrophoresis (SDS-PAGE) to prepare a solution of cells at OD600 nm=20. The prepared solution was subject to 5-20% polyacrylamide gel SDS-PAGE and then CBB staining was carried out to compare an expression level of Knob-5134 between with and without addition of APSP. As a result, *E. coli* cells obtained by transformation with pET-ALP-S134 having a modified APSP exhibited an increased expression level as compared to *E. coli* cells obtained by transformation with pET15b-S134 in which APSP is not added or with pET-nALP-5134 having a non-modified APSP (cf. FIG. 5).

INDUSTRIAL APPLICABILITY

A process for preparing a protein that forms an inclusion body when expressed in prokaryotic cells in accordance with the present invention may be utilized for efficiently producing various exogenous, industrially useful proteins in *E. coli*. In particular, the process may suitably be used for the production of pro-matrix metalloprotease 7, a precursor of matrix metalloprotease 7.

The invention claimed is:

1. A nucleic acid fragment consisting of a nucleotide sequence coding for a protein that forms an inclusion body when expressed in prokaryotic cells (inclusion body-forming protein), said fragment comprising a nucleotide sequence coding for a signal peptide and a nucleotide sequence coding for a protein of interest,
wherein the signal peptide consists of the sequence of SEQ ID NO: 1 with:
(i) a substitution of leucine at the 13th position with any one of the amino acids selected from the group consisting of proline, phenylalanine and tryptophan, or
(ii) a substitution of leucine at the 13th position as set forth in (i) and a substitution of alanine at the 21st position with any one of the amino acids selected from the group consisting of aspartic acid, glutamic acid, lysine, histidine, phenylalanine and tyrosine.

2. The nucleic acid fragment of claim 1 wherein said prokaryotic cells are Gram negative bacteria.

3. The nucleic acid fragment of claim 1 wherein said prokaryotic cells are *E. coli*.

4. The nucleic acid fragment of claim 1 wherein said protein of interest is the pro-matrix metalloprotease 7 (proMMP-7) set forth by SEQ ID NO: 22.

5. The nucleic acid fragment of claim 1 wherein the nucleotide sequence coding for the protein of interest is downstream of the nucleotide sequence coding for the signal peptide.

6. An expression vector comprising the nucleic acid fragment of claim 1.

7. A host producing an inclusion body-forming protein obtained by transforming a host with the expression vector as set forth in claim 6.

8. The host producing an inclusion body-forming protein of claim 7 wherein the host is prokaryotic cells.

9. The host producing an inclusion body-forming protein of claim 7 wherein the host is Gram negative bacteria.

10. The host producing an inclusion body-forming protein of claim 7 wherein the host is *E. coli*.

11. A process for preparing a protein that forms an inclusion body when expressed in prokaryotic cells (an inclusion body-forming protein), the process consisting of (1) to (3):
(1) preparing an expression vector comprising the nucleic acid fragment of claim 1,
(2) preparing a host cell transformed with the expression vector of (1) above that produces an inclusion body-forming protein, and
(3) purifying the inclusion body-forming protein from culture obtained by culturing the host cell of (2) above that produces the inclusion body-forming protein.

12. The process of claim 11 wherein said expression vector is an expression vector where the nucleic acid fragment is incorporated downstream of a T7 promoter.

13. The process of claim 11 wherein the host is prokaryotic cells.

14. The process of claim 11 wherein the host is Gram negative bacteria.

15. The process of claim 11 wherein the host is *E. coli*.

16. The process of claim 11 wherein the host cell that produces the inclusion body-forming protein is cultured in an antibiotic-free culture medium.

* * * * *

SEQUENCE LISTING

```
<160> NUMBER OF SEQ ID NOS: 23

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1

Met Lys Gln Ser Thr Ile Ala Leu Ala Leu Leu Pro Leu Leu Phe Thr
1               5                   10                  15

Pro Val Thr Lys Ala
            20

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccataggtcc aagaacaatt gtctctg                                         27

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caatccaatg aatgaatgaa tggatg                                          26

<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catatgaaac aaagcactat tgcactggca ctcttaccgt tactgtttac ccctgtgacc     60
aaggccctgc cgctgcctca g                                               81

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggatccctat ttctttcttg aattac                                          26

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cttggtcaca ggggtaaaca gtaacggtaa ga                                   32

<210> SEQ ID NO 7
<211> LENGTH: 33
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
cttggtcaca ggggtaaaca gtggcggtaa gag                                   33

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggtaagagt gccagtgcaa tagtgctttg tttc                                  34

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgtttaccc ctgtgaccaa ggatctgccg ctgcc                                 35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctgtttaccc ctgtgaccaa ggaactgccg ctgcc                                 35

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctgtttaccc ctgtgaccaa gaaactgccg ctgcc                                 35

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgcactggc actcttaccg ccgctgttta cccctg                                36

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 13
ctgtttaccc ctgtgaccaa gcatctgccg ctgcc                                35

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctgtttaccc ctgtgaccaa gtttctgccg ctgcc                                35

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctgtttaccc ctgtgaccaa gtatctgccg ctgcc                                35

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caaccatgga aggagaggtg gaaatta                                         27

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgcggatccc taaccttgag tgctagatgc tgtaggtgc                            39

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgcggatcca ctaattataa tgacaaa                                         27

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 19
ggaagatctc taaccttgag tgctagatgc                                        30

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ser Arg Pro Arg Leu Ile Val Ala Leu Phe Leu Phe Phe Asn Val
1               5                   10                  15

Phe Val His Gly Glu Asn Lys Val Lys Gln Ser Thr Ile Ala Leu Ala
            20                  25                  30

Leu Leu Pro Leu Leu Phe Thr Pro Val Thr Lys Ala
        35                  40

<210> SEQ ID NO 21
<211> LENGTH: 750
<212> TYPE: DNA
<213> ORGANISM: Homo sapiens

<400> SEQUENCE: 21
ctgccgctgc ctcaggaggc gggaggcatg agtgagctac agtgggaaca ggctcaggac        60
tatctcaaga gatttttatct ctatgactca gaaacaaaaa atgccaacag tttagaagcc     120
aaactcaagg agatgcaaaa attctttggc ctacctataa ctggaatgtt aaactcccgc      180
gtcatagaaa taatgcagaa gcccagatgt ggagtgccag atgttgcaga atactcacta      240
tttccaaata gcccaaaatg gacttccaaa gtggtcacct acaggatcgt atcatatact      300
cgagacttac cgcatattac agtggatcga ttagtgtcaa aggctttaaa catgtggggc      360
aaagagatcc ccctgcattt caggaaagtt gtatggggaa ctgctgacat catgattggc      420
tttgcgcgag gagctcatgg ggactcctac ccatttgatg gccaggaaa cacgctggct       480 catgcctttg cgcctgggac aggtctcgga ggagatgctc acttcgatga ggatgaacgc      540
tggacggatg gtagcagtct agggattaac ttcctgtatg ctgcaactca tgaacttggc      600
cattctttgg gtatgggaca ttcctctgat cctaatgcag tgatgtatcc aacctatgga      660
aatggagatc cccaaaattt taaactttcc caggatgata ttaaaggcat tcagaaacta      720 tatgaaaga gaagtaattc aagaaagaaa                                        750

<210> SEQ ID NO 22
<211> LENGTH: 173
<212> TYPE: PRT
<213> ORGANISM: Homo sapiens

<400> SEQUENCE: 22

Tyr Ser Leu Phe Pro Asn Ser Pro Lys Trp Thr Ser Lys Val Val Thr
1               5                   10                  15

Tyr Arg Ile Val Ser Tyr Thr Arg Asp Leu Pro His Ile Thr Val Asp
            20                  25                  30

Arg Leu Val Ser Lys Ala Leu Asn Met Trp Gly Lys Glu Ile Pro Leu
        35                  40                  45

His Phe Arg Lys Val Val Trp Gly Thr Ala Asp Ile Met Ile Gly Phe
    50                  55                  60

Ala Arg Gly Ala His Gly Asp Ser Tyr Pro Phe Asp Gly Pro Gly Asn
65                  70                  75                  80
```

```
Thr Leu Ala His Ala Phe Ala Pro Gly Thr Gly Leu Gly Gly Asp Ala
            85                  90                  95

His Phe Asp Glu Asp Glu Arg Trp Thr Asp Gly Ser Ser Leu Gly Ile
                100                 105                 110

Asn Phe Leu Tyr Ala Ala Thr His Glu Leu Gly His Ser Leu Gly Met
            115                 120                 125

Gly His Ser Ser Asp Pro Asn Ala Val Met Tyr Pro Thr Tyr Gly Asn
        130                 135                 140

Gly Asp Pro Gln Asn Phe Lys Leu Ser Gln Asp Ile Lys Gly Ile
145                 150                 155                 160

Gln Lys Leu Tyr Gly Lys Arg Ser Asn Ser Arg Lys Lys
                165                 170

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Arg

<400> SEQUENCE: 23

Pro Leu Gly Leu Trp Ala Arg
1               5
```